(12) United States Patent
Malkova et al.

(10) Patent No.: US 9,595,481 B1
(45) Date of Patent: Mar. 14, 2017

(54) DISPERSION MODEL FOR BAND GAP TRACKING

(71) Applicant: KLA-Tencor Corporation, Milpitas, CA (US)

(72) Inventors: Natalia Malkova, Hayward, CA (US); Leonid Poslavsky, Belmont, CA (US); Ming Di, Hayward, CA (US); Qiang Zhao, Milpitas, CA (US); Dawei Hu, Shanghai (CN)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/464,640

(22) Filed: Aug. 20, 2014

Related U.S. Application Data

(60) Provisional application No. 61/869,493, filed on Aug. 23, 2013.

(51) Int. Cl.
*H01L 21/66* (2006.01)
*G01R 31/26* (2014.01)
*G01N 21/95* (2006.01)

(52) U.S. Cl.
CPC ......... *H01L 22/12* (2013.01); *G01N 21/9501* (2013.01); *G01R 31/2601* (2013.01)

(58) Field of Classification Search
None
See application file for complete search history.

(56) References Cited

U.S. PATENT DOCUMENTS

| | | | |
|---|---|---|---|
| 6,465,265 | B2 | 10/2002 | Opsal et al. |
| 7,239,391 | B2 | 7/2007 | Synowicki et al. |
| 7,414,721 | B1 | 8/2008 | Suvkhanov et al. |
| 8,711,349 | B2 | 4/2014 | Gao et al. |
| 2010/0068834 | A1 | 3/2010 | Hachigo et al. |

OTHER PUBLICATIONS

Sancho-Parramon et al., "Optical characterization of HfO2 by spectroscopic ellipsometry: Dispersion models and direct data inversion," 2008, Thin Solid Films, 516, pp. 7990-7995.*

(Continued)

*Primary Examiner* — Kimberly Rizkallah
*Assistant Examiner* — Bo Bin Jang
(74) *Attorney, Agent, or Firm* — Spano Law Group; Joseph S. Spano

(57) ABSTRACT

Methods and systems for determining band structure characteristics of high-k dielectric films deposited over a substrate based on spectral response data are presented. High throughput spectrometers are utilized to quickly measure semiconductor wafers early in the manufacturing process. Optical models of semiconductor structures capable of accurate characterization of defects in high-K dielectric layers and embedded nanostructures are presented. In one example, the optical dispersion model includes a continuous Cody-Lorentz model having continuous first derivatives that is sensitive to a band gap of a layer of the unfinished, multi-layer semiconductor wafer. These models quickly and accurately represent experimental results in a physically meaningful manner. The model parameter values can be subsequently used to gain insight and control over a manufacturing process.

20 Claims, 5 Drawing Sheets

(56) References Cited

OTHER PUBLICATIONS

Price et al., "Spectroscopic ellipsometry characterization of HfxSiyOz films using the Cody-Lorentz parametrized model," 2004, Applied Physics Letters, 85(10), pp. 1701-1703.*

He, G., et al., "Thickness-modulated Optical Dielectric Constants and Band Alignments of HfOxNy Gate Dielectrics," Journal of Applied Physics, Jan. 14, 2009, 105, 014109, pp. 1-4, USA.

Price, J., et al., "Identification of Interfacial Defects in High-k Gate Stack Films by Spectroscopic Ellipsometry," Journal of Vacuum Science and Technology, American Vacuum Society, Feb. 9, 2009, B 27(1), pp. 310-312, USA.

Price, J., et al., "Identification of Sub-Band-Gap Absorption Features at the HfO2/Si(100) Interface Via Spectroscopic Ellipsometry," Applied Physics Letters, American Institute of Physics, Aug. 10, 2007, 91, 061925, pp. 1-3, USA.

* cited by examiner

DISPERSION MODEL FOR BAND GAP TRACKING

CROSS REFERENCE TO RELATED APPLICATION

The present application for patent claims priority under 35 U.S.C. §119 from U.S. provisional patent application Ser. No. 61/869,493, entitled "Dispersion Model For Band Gap Tracking," filed Aug. 23, 2013, the subject matter of which is incorporated herein by reference.

TECHNICAL FIELD

The described embodiments relate to systems for wafer inspection, and more particularly to characterization of thin films used in semiconductor manufacturing.

BACKGROUND INFORMATION

Semiconductor devices such as logic and memory devices are typically fabricated by a sequence of processing steps applied to a substrate or wafer. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Inspection processes are used at various steps during a semiconductor manufacturing process to detect defects on wafers to promote higher yield. As design rules and process windows continue to shrink in size, inspection systems are required to capture a wider range of physical defects on wafer surfaces while maintaining high throughput.

Semiconductor devices are increasingly valued based on their energy efficiency, rather than speed alone. For example, energy efficient consumer products are more valuable because they operate at lower temperatures and for longer periods of time on a fixed battery power supply. In another example, energy efficient data servers are in demand to reduce their operating costs. As a result, there is a strong interest to reduce the energy consumption of semiconductor devices.

Leakage current through insulator layers is a major energy loss mechanism of semiconductor devices manufactured at the 65 nm technology node and below. In response, electronic designers and manufacturers are adopting new materials (e.g., hafnium silicate (HfSiO4), nitrided hafnium silicates (HfSiON), hafnium dioxide (HfO2), zirconium silicate (ZrSiO4), etc.) with higher dielectric constants than traditional materials (e.g., silicon dioxide). These "high-k" materials reduce leakage current and enable the manufacture of smaller sized transistors.

Along with the adoption of new dielectric materials, the need has arisen for measurement tools to characterize the dielectric properties and band structures of high-k materials early in the manufacturing process. More specifically, high throughput monitoring tools are required to monitor and control the deposition of high-k materials during wafer manufacture to ensure a high yield of finished wafers. Early detection of deposition problems is important because the deposition of high-k materials is an early process step of a lengthy and expensive manufacturing process. In some examples, a high-k material is deposited on a wafer at the beginning of a manufacturing process that takes over one month to complete.

The performance of a logic gate is commonly characterized in terms of electrical characteristics such as equivalent oxide thickness (EOT), leakage current, threshold voltage, leakage EOT, and breakdown voltage. During device processing it is important to monitor and control these parameters. These electrical characteristics may be studied by a variety of methods including electrical measurements, transmission electron microscopy, x-ray spectroscopy and scattering, atomic force microscopy, and photoelectronic spectroscopy. Currently, however, these measurement technologies suffer from any of a number of limitations. In some cases, the measurements require destruction of the sample. In some cases, many post-deposition processing steps must be completed before measurements can occur. In some cases, the measurement technology is slow, and must be separated from the production line.

Optical metrology tools offer the possibility of high throughput, in-line, non-destructive characterization of electrical characteristics of gate structures. In particular, the spectroscopic ellipsometry (SE) measurement technique includes a parametric representation of a measured optical dispersion. In some examples, the parameterized model is representative of a dielectric function that has a direct relation to the band gap parameter; a key indicator of the electrical performance of the gate structure. In general, the particular parameterization is selected to reduce the number of unknown parameters and decrease correlations among parameters.

In some examples, the optical response of one or more high-K dielectric layers is predicted based on a direct inversion method. These methods are described by way of example in J. Price et al., "Identification of interfacial defects in high-k gate stack films by spectroscopic ellipsometry," J. Vac. Sci. Technol. B 27 (1), 310 (2009) and J. Price et al., "Identification of sub-band-gap absorption features at the HfO2/Si(100) interface via spectroscopic ellipsometry," APL 91, 061925 (2007), the subject matter of each is incorporated herein in its entirety. However, direct inversion methods are computationally burdensome, very sensitive to statistical measurement errors, and do not provide a physically based model of the measured structure (i.e., the optical functions do not satisfy the Kramers-Kronig consistency condition). As a result, the utility of direct inversion methods for high-throughput inspection and process control is limited. In addition, the direct inversion method involves an ill-defined mathematical problem. SE measurements provide two values (e.g., $\alpha$ and $\beta$, $\Psi$ and $\Delta$, etc.) for each measured wavelength, but the model inversion must generate estimates for three unknowns. For example, the inversion might provide estimates for the real ($\in_1$) and imaginary ($\in_2$) parts of the dielectric function and film thickness. In another example, the inversion might provide estimates for the refractive index (n) and extinction coefficient (k) and film thickness. The solution to this ill-defined problem requires the introduction of artificial, simplifying assumptions that introduce undesirable errors.

In some other examples, the optical response of one or more high-K dielectric layers is predicted based on a Bruggeman Effective Model Approximation (BEMA) model. The BEMA model represents the dielectric function of the layer as an effective composition of assumed dielectric functions of constituents. The optimized effective composition is then related to the composition of the dielectric layer of interest. In general, the BEMA model is based on Kramers-Kronig consistent dielectric functions of constituents, and thus is itself Kramers-Kronig consistent. As a result, the BEMA model yields physically reasonable results. However, the value of the band gap as derived from the BEMA model is an indirect measurement that requires a reference to provide meaningfully accurate results.

Both the BEMA and the direct inversion method are used to extract dispersion curves (e.g., the real ($\in_1$) and the imaginary ($\in_2$) parts of the dielectric function, or refractive index (n) and extinction coefficient (k)) from SE measurements. Subsequently, the calculated dispersion curves must be interpolated in the energy range of interest to evaluate the band gap. The accuracy of the band gap estimate depends strongly on the choice of the energy of interest for band gap interpolation. Moreover, since band gap must be indirectly derived from the calculated dispersion curves, a reference is required to provide accurate results. For these practical reasons, both BEMA and direct inversion are limited in their ability to accurately monitor band gap.

In some other examples, a Tauc-Lorentz model or a Cody-Lorentz model is employed as described by way of example in A. S. Ferlauto et al., "Analytical model for the optical functions of amorphous semiconductors from the near-infrared to ultraviolet: Application in thin film photovoltaics," J. Appl. Phys. 92, 2424 (2002), the subject matter of which is incorporated herein in its entirety. In these models, the imaginary part of the dielectric function is represented by a parameterized dispersion function, and the real part of the dielectric function is determined based on enforcement of Kramers-Kronig consistency. Model parameters (e.g., optical function parameters and thicknesses) are evaluated by fitting modeled spectra to measured spectra by numerical regression. The validity and limitations of the models are assessed by statistical evaluation of fitting quality and confidence limits of model parameters.

An important limitation of the conventional Cody-Lorentz function is that it has discontinuous derivatives over the energy range, E, and the resonant energy range, $E_0$, at the Urbach transition energy level, $E_T$. This leaves the dispersion model mathematically ill-defined, leaving open the possibility that the model will yield results that have no relation to real, physical features of the material. Moreover, continuity of derivatives is an important characteristic of any optical model subject to optimization in SE metrology. In particular, a discontinuity of derivatives may make the optimization process computationally unstable.

Accordingly, it would be advantageous to develop high throughput methods and/or systems for characterizing high-k dielectric layers early in the manufacturing process. In particular, it would be advantageous to develop a robust, reliable, and stable approach to in-line SE metrology of gate stacks including high-K dielectrics.

SUMMARY

Methods and systems for determining band structure characteristics of high-k dielectric films deposited over a substrate based on spectral response data are presented. Optical models of semiconductor structures such as gate dielectric stacks are presented. In particular, models capable of accurate characterization of band gap in high-K dielectric layers and nanostructures based on high-K dielectric materials are described. These models quickly and accurately represent experimental results in a physically meaningful manner that can be subsequently used to gain insight and control over a manufacturing process.

In one aspect, the selected dispersion model includes a modified Cody-Lorentz model constrained to have continuous first derivatives to describe the complex bulk band structure of high-K dielectric layers. In a further aspect, a band structure characteristic indicative of an electrical performance of the measured layer, or stack of layers, is determined based at least in part on the parameter values of the optical dispersion model of the multi-layer semiconductor wafer. In some embodiments, the optical band gap is determined based at least in part on the parameter values of the optical dispersion model of the multi-layer semiconductor wafer. Moreover, the optical band gap is shown to be highly correlated with leakage current. Thus, the electrical performance of unfinished semiconductor devices is accurately predicted based on accurate estimates of the optical band gap derived from measurements of the target layer, or stack of layers, and the measurement models described herein.

In another further aspect, device performance is improved by controlling a process of manufacture of the semiconductor wafer based at least in part on the identified band structure characteristic. In one example, layer thickness may be controlled based on band gap characteristics identified from the parameter values of the optical dispersion model.

The foregoing is a summary and thus contains, by necessity, simplifications, generalizations, and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Optical models of semiconductor structures such as gate dielectric stacks are presented. In particular, models capable of accurate characterization of band structure characteristics in high-K dielectric layers and nanostructures based on high-K dielectric materials are presented. These models quickly and accurately represent experimental results in a physically meaningful manner that can be subsequently used to gain insight and control over a manufacturing process.

Figure 1:
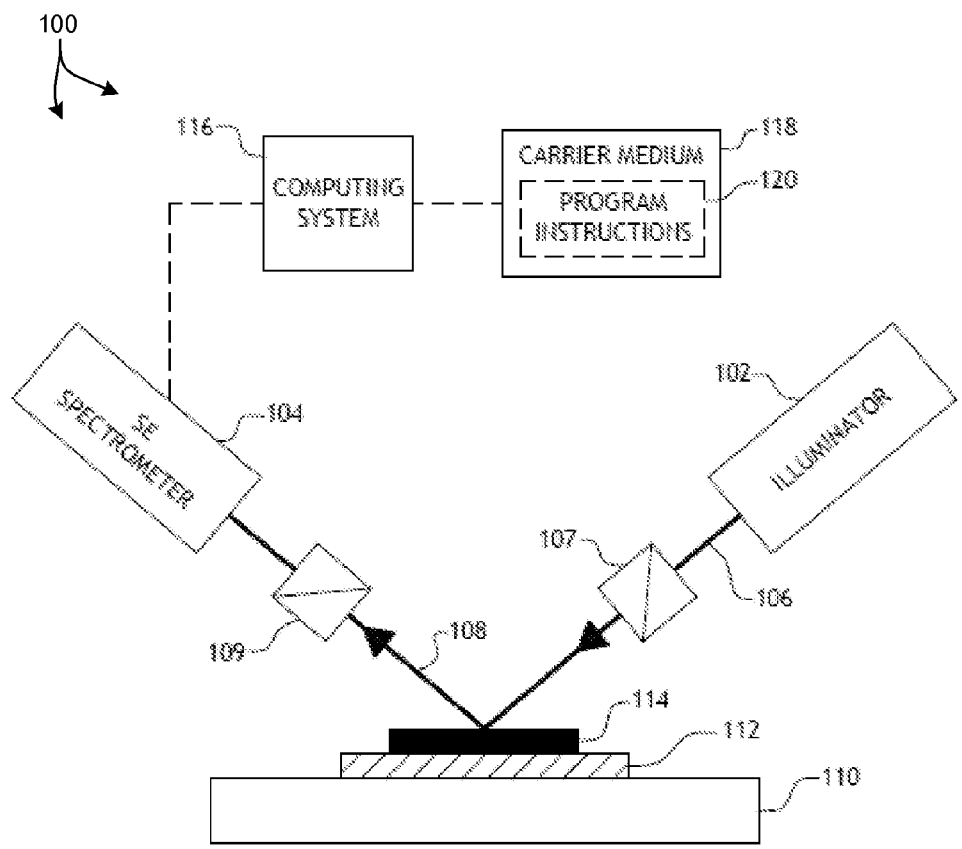
FIG. 1 is a simplified diagram illustrative of a wafer inspection system 100 including thin film characterization functionality.

FIG. 1 illustrates a system 100 for measuring a spectral response of a thin film of a semiconductor wafer, in accordance with one embodiment of the present invention. As shown in FIG. 1, the system 100 may be used to perform spectroscopic ellipsometry on one or more films 114 of a semiconductor wafer 112 disposed on a translation stage 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-850 nm) to the thin film (e.g., HfSiON thin film) disposed on the surface of the semiconductor wafer 112. In turn, the spectrometer 104 is configured to receive illumination reflected from the surface of the semiconductor wafer 112. It is further noted that the light emerging from the illuminator 102 is polarized using polarizer 107 to produce a polarized illumination beam 106. The radiation reflected by the thin film 114 disposed on the wafer 112 is passed through an analyzer 109 and to the spectrometer 104. In this regard, the radiation received by the spectrometer 104 in the collection beam 108 is compared to the incident radiation of the illumination beam 106, allowing for spectral analysis of the thin film 114.

In a further embodiment, the system 100 may include one or more computing systems 116. The one or more computing systems 116 may be communicatively coupled to the spectrometer 104. In one aspect, the one or more computing systems 116 may be configured to receive a set of spectral measurements performed by the spectrometer 104 on one or more wafers. Upon receiving results of the one or more sampling process from the spectrometer, the one or more computing systems 116 may then calculate parameters of an optical dispersion model. In this regard, the computing system 116 may extract the real component (n) and the imaginary component (k) of the complex index of refraction of the thin film across the selected spectral range (e.g., 150-850 nm) for the acquired spectrum from the spectrometer 104. Further, the computing system 116 may extract the n- and k-curves utilizing a regression process (e.g., ordinary least squares regression) applied to a selected dispersion model. In a preferred embodiment, the selected dispersion model is a continuous Cody-Lorentz model as described herein.

In a further embodiment, the computing system 116 may determine a band structure characteristic indicative of a defect of the film 114 based on parameter values of the optical dispersion model. For example, the computing system 116 may be configured to automatically identify defects from parameter values of the optical dispersion model.

In another further embodiment, the computing system 116 may control a process of manufacture a semiconductor wafer based at least in part on a band structure characteristic determined from parameter values of the optical dispersion model. For example, computing system 116 may be configured to communicate process control parameter values to one or more manufacturing tools responsible for the manufacture of the semiconductor wafers being measured.

Figure 2:
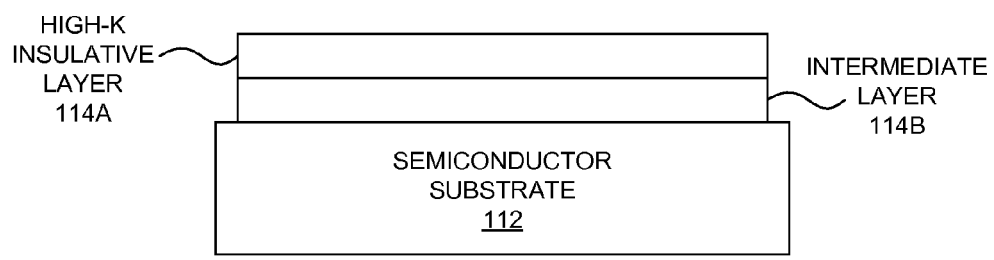
FIG. 2 is a simplified diagram illustrative of a semiconductor substrate 112 with attached thin film layers 114A and 114B that may be characterized by methods and systems as described herein.

As illustrated in FIG. 2, in some embodiments, an intermediate layer 114B is located between a semiconductor substrate 112 (e.g., silicon) and a high-k insulative layer 114A to promote adhesion between the high-k material and the semiconductor substrate. Typically, the intermediate layer 114B is very thin (e.g., ten Angstroms). In some examples, the high-k insulative layer 114A and the intermediate layer 114B are modeled together as one layer for purposes of analysis employing the methods and systems as described herein. In this example, the one or more computing systems 116 may determine one or more parameters of an optical dispersion model of the film layer 114 including both the intermediate layer 114B and high-k insulative layer 114A. However, in some other examples, each layer may be modeled separately. In this example, the one or more computing systems 116 may determine one or more parameters of an optical dispersion model of the high-k insulative layer 114A and one or more parameters of an optical dispersion model of the intermediate layer 114B film layer.

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described above. Therefore, the above description should not be interpreted as a limitation on the present invention but merely an illustration. Further, the one or more computing systems 116 may be configured to perform any other step(s) of any of the method embodiments described herein.

In another embodiment, the computer system 116 may be communicatively coupled to the spectrometer 104 or the illuminator subsystem 102 of the ellipsometer 101 in any manner known in the art. For example, the one or more computing systems 116 may be coupled to a computing system of the spectrometer 104 of the ellipsometer 101 and a computing system of the illuminator subsystem 102. In another example, the spectrometer 104 and the illuminator 102 may be controlled by a single computer system. In this manner, the computer system 116 of the system 100 may be coupled to a single ellipsometer computer system.

The computer system 116 of the system 100 may be configured to receive and/or acquire data or information from the subsystems of the system (e.g., spectrometer 104, illuminator 102, and the like) by a transmission medium that may include wireline and/or wireless portions. In this manner, the transmission medium may serve as a data link between the computer system 116 and other subsystems of the system 100. Further, the computing system 116 may be configured to receive spectral results via a storage medium (i.e., memory). For instance, the spectral results obtained using a spectrometer of an ellipsometer may be stored in a permanent or semi-permanent memory device. In this regard, the spectral results may be imported from an external system.

Moreover, the computer system 116 may send data to external systems via a transmission medium. Moreover, the computer system 116 of the system 100 may be configured to receive and/or acquire data or information from other systems (e.g., inspection results from an inspection system or metrology results from a metrology system) by a transmission medium that may include wireline and/or wireless portions. In this manner, the transmission medium may serve as a data link between the computer system 116 and other subsystems of the system 100. Moreover, the computer system 116 may send data to external systems via a transmission medium.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

The embodiments of the system 100 illustrated in FIG. 1 may be further configured as described herein. In addition, the system 100 may be configured to perform any other step(s) of any of the method embodiment(s) described herein.

Figure 3:
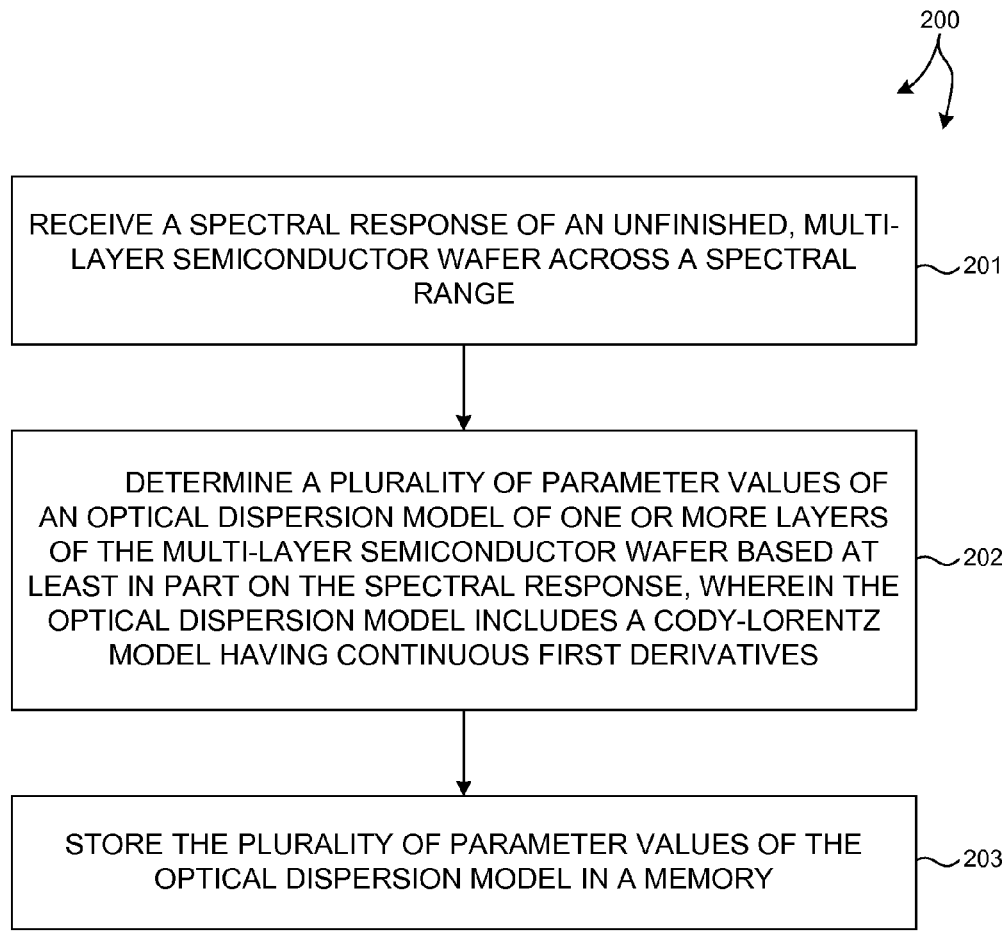
FIG. 3 is a flowchart illustrative of a method 200 of determining parameter values of a continuous Cody-Lorentz model from spectral response data.

FIG. 3 illustrates a process flow 200 suitable for implementation by the system 100 of the present invention. In one aspect, it is recognized that data processing steps of the process flow 200 may be carried out via a pre-programmed algorithm executed by one or more processors of computing system 116. While the following description is presented in the context of system 100, it is recognized herein that the particular structural aspects of system 100 do not represent limitations and should be interpreted as illustrative only.

In block 201, a spectral response of an unfinished, multi-layer semiconductor wafer across a broad spectral range is received after a high-k thin film is deposited on the wafer. For example, spectra may be received from an ellipsometer 101. In another example, spectra may be received from a reflectometer (not shown). The spectral data may be acquired from each of the thin films 114 deposited on the wafer 112 utilizing the spectroscopic ellipsometer 101. For instance, the ellipsometer 101 may include an illuminator 102 and a spectrometer 104, as discussed previously herein. The spectrometer 104 may transmit results associated with a spectroscopic measurement of the thin films of the wafer to one or more computing systems 116 for analysis. In another example, the spectra for multiple thin films 114 may be acquired by importing previously obtained spectral data. In this regard, there is no requirement that the spectral acquisition and the subsequent analysis of the spectral data need be contemporaneous or performed in spatial proximity. For instance, spectral data may be stored in memory for analysis at a later time. This may be desirable, for example, for diagnostic purposes, or analysis of large sets of measurement data. In another instance, spectral results may be obtained and transmitted to an analysis computing system located at a remote location.

In block 202, a plurality of parameter values of an optical dispersion model of one or more layers of the multi-layer semiconductor wafer are determined based at least in part on the spectral response. In one example, the optical dispersion model includes a Cody-Lorentz model having continuous first derivatives that is sensitive to one or more defects of the unfinished, multi-layer semiconductor wafer.

In general, the optical dispersion model as described herein may be configured to characterize any useful optical dispersion metric. For example, any of the real (n) and imaginary (k) components of the complex index of refraction may be characterized by the optical dispersion model. In another example, any of the real ($\epsilon_1$) and imaginary ($\epsilon_2$) components of the complex dielectric constant may be characterized by the optical dispersion model. In other examples, any of the square root of $\epsilon_2$, absorption constant $\alpha = 4\eta k/\lambda$, conductivity ($\sigma$), skin depth ($\delta$), and attenuation constant $(\sigma/2)*\text{sqrt}(\mu/\epsilon)$, where $\mu$ is the free space permeability, may be characterized by the optical dispersion model. In other examples, any combination of the aforementioned optical dispersion metrics may be characterized by the optical dispersion model. The aforementioned optical dispersion metrics are provided by way of non-limiting example. Other optical dispersion metrics or combinations of metrics may be contemplated.

In one example, the parameter values of an optical dispersion model of the real ($\epsilon_1$) and imaginary ($\epsilon_2$) components of the complex dielectric constant across the selected spectral range are determined utilizing a regression process. In this regard, a regression method may be applied to the measured spectral data using a selected dispersion model.

In one aspect, the selected dispersion model includes a continuous Cody-Lorentz model having continuous first derivatives to describe the complex bulk band structure of high-K dielectric layer. In one example, the imaginary part of the dielectric function, $\epsilon_2(E)$, is defined by Equation (1).

$$\varepsilon_2(E) = \frac{E_1}{E}\exp\left(\frac{E-E_t}{E_u}\right), \quad 0 < E < E_t \qquad (1)$$
$$= G_C(E)L(E), \qquad E \geq E_t$$

In the energy range, $0 < E < E_t$, equation (1) describes the Urbach tails with an exponential function where $E_t$ is the Urbach transition energy, $E_u$ is the rate of attenuation of the Urbach function, and $E_1$ is the amplitude of the Urbach function. In the energy range, $E \geq E_t$, the Cody-Lorentz function is defined as the Lorentz function, $L(E)$, modulated by a gap function used to describe the band-edge of amorphous dielectrics. The gap function is described by equation (2), $$G_c(E) = \frac{(E-E_g)^2}{(E-E_g)^2 + E_p^2} \qquad (2)$$

where $E_g$ is the band gap and $E_p$ is the transition energy. The Lorenz function is described by equation (3), $$L(E) = \frac{AE_0 \Gamma E}{(E_0^2 - E^2)^2 + \Gamma^2 E^2} \qquad (3)$$

where A is the amplitude of the Lorentz peak describing the optical response, $E_0$ is the resonant energy of the Lorentz function describing the optical response, and $\Gamma$ is the width of the Lorentz function describing the optical response.

The amplitude of the Urbach function, $E_1$, is defined to enforce continuity of the dielectric function (1) at the demarcation energy, $E_t$, as described by equation (4).

$$E_1 = E_t G_C(E_t) L(E_t) \qquad (4)$$

The conventional Cody-Lorentz model formulation constrains the main characteristic energies of the model such that $E_g \leq E_t < E_0$. This implies that the transition energy, $E_t$, between the Urbach tails and the gap region cannot be smaller than the band gap energy, $E_g$, and cannot be larger than the resonant energy, $E_0$, where the resonant energy corresponds approximately to the maximum of the absorption band. Moreover, the rate of attenuation of the Urbach tail is constrained to be non-negative, $E_u \geq 0$.

Figure 4:
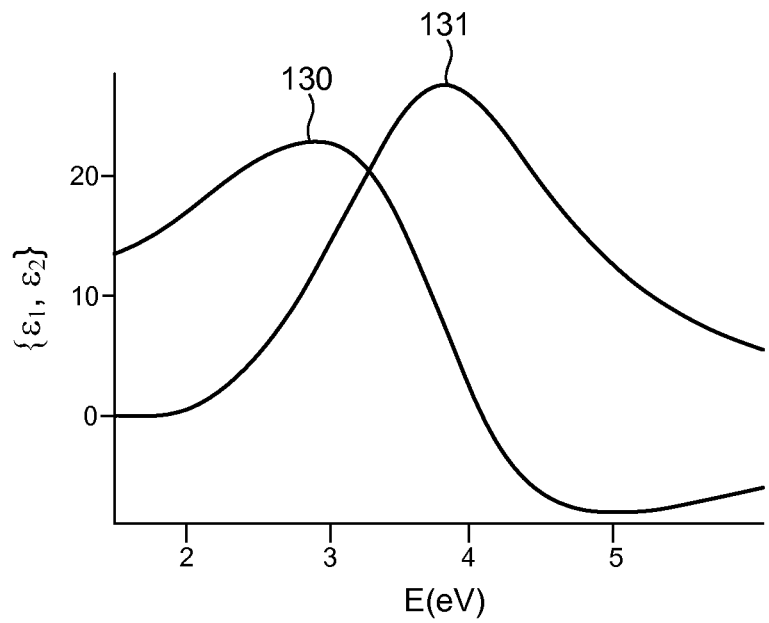
FIG. 4 is a plot illustrative of the real and imaginary parts of a dielectric function of a thin film sample based on a conventional Cody-Lorentz model.
Figure 5:
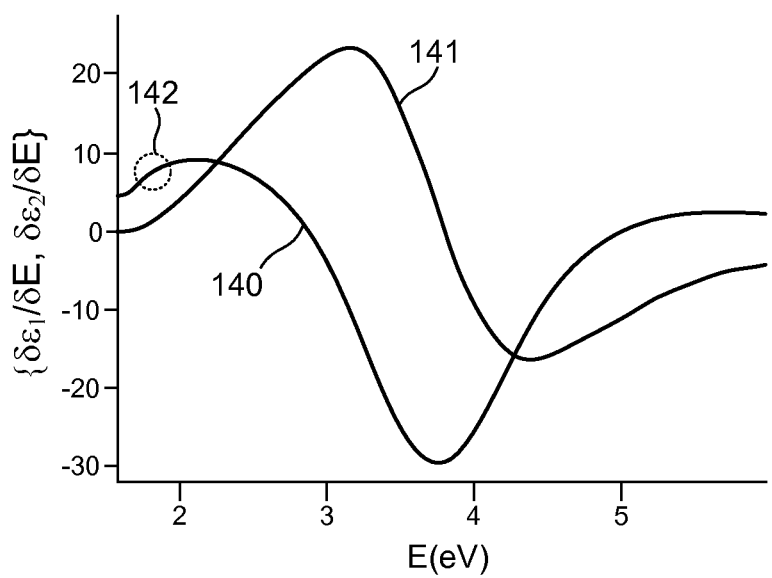
FIG. 5 is a plot illustrative of the first derivatives of the real and imaginary parts the dielectric function of a thin film sample based on a conventional Cody-Lorentz model.
Figure 6:
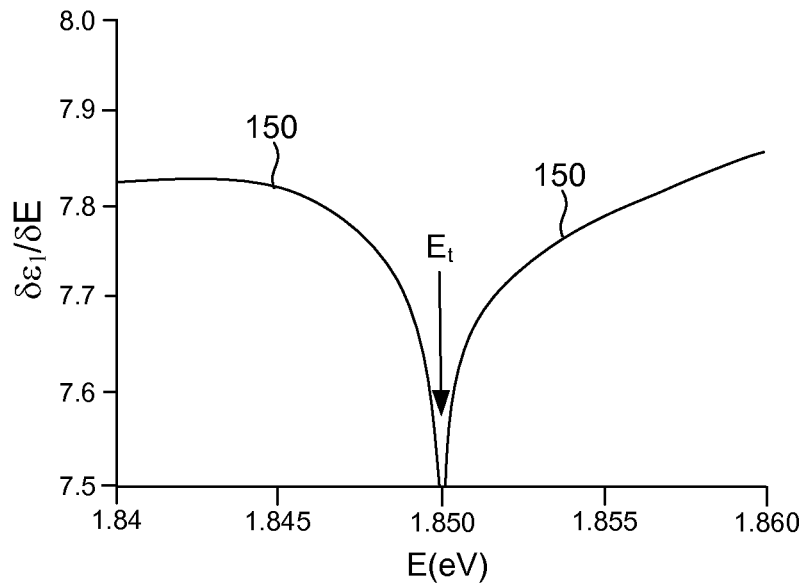
FIG. 6 is a plot illustrative of the region 142 highlighted in FIG. 5, including a discontinuity in the first derivative of the real part of the dielectric function of a thin film sample based on a conventional Cody-Lorentz model.

FIG. 4 is a plot 130 of the real part of the dielectric function, $\in_1(E)$, and a plot 131 of the imaginary part of the dielectric function, $\in_2(E)$, as determined based on a conventional Cody-Lorentz model formulation. FIG. 5 is a plot 140 of the derivative of the real part of the dielectric function, $\delta\in_1/\delta E$, and a plot 141 of the derivative of the imaginary part of the dielectric function, $\delta\in_2/\delta E$, derived from the dielectric functions $\in_1(E)$ and $\in_2(E)$ illustrated in FIG. 4. An important limitation of the conventional Cody-Lorentz model formulation is that it has discontinuous derivatives over energy, E, and resonant energy, $E_0$ at the transition energy, $E_t$. The region of this discontinuity is highlighted by dashed circle 142. This region is highlighted in FIG. 6. FIG. 6 illustrates a plot 150 of the derivative of the real part of the dielectric function, $\delta\in_1/\delta E$, pictured in FIG. 5 over the region highlighted by dashed circle 142. As illustrated in FIG. 6, the derivative is discontinuous at the transition energy, $E_t$.

In one aspect, the dispersion function defined by Equations (1)-(4) is constrained such that the constrained dispersion function has continuous derivatives over E and $E_0$ at the transition energy, $E_t$. In one example, the rate of attenuation of the Urbach function, $E_u$, is defined by equation (5), $$E_u = \frac{E_1}{\partial E_1 / \partial E_t} = \frac{E_1}{D} \quad (5)$$

where, $$D = \frac{E_0^4 - E_t^4}{(E_0^2 - E_t^2)^2 + \Gamma^2 E_t^2} + \frac{E_p^2}{(E_t - E_g)^2 + E_p^2} \cdot \frac{E_t}{E_t - E_g} \quad (6)$$

As a result, the continuous Cody-Lorentz model includes six fitting parameters in terms of energy, $\{E_g, E_p, A, E_0, \Gamma, E_t\}$, provided that $E_u$ is defined by Eq. (6). Furthermore, as follows directly from equation (6), $E_u$ is constrained to be a non-negative value within the transition energy range $E_g \leq E_t < E_0$. Therefore, the continuous Cody-Lorentz model is intrinsically well-defined and physically meaningful.

The real part of the dielectric function, $\in_1(E)$, is determined by enforcing Kramers-Kronig consistency to arrive at the following expression for $\in_1(E)$:

$$\varepsilon_1(E) = \varepsilon_1(\infty) + \frac{2}{\pi} P \int_0^\infty \frac{\xi \varepsilon_2(\xi)}{\xi^2 - E^2} d\xi \quad (7)$$

where $\in_1(\infty)$ is the high frequency electron component of the dielectric constant and P is the principal value of the integral. Equation (7) can be reformulated from its integral form to an analytical expression as follows:

$$\varepsilon_1(E) = \varepsilon_1(\infty) + I_U(E) + \sum_{n=1:8} (X_n \varphi_n) \quad (8)$$

where $I_u(E)$ is the Urbach integral and $X_n$ and $\phi_n$ are well-defined functions of the model parameters.

Figure 7:
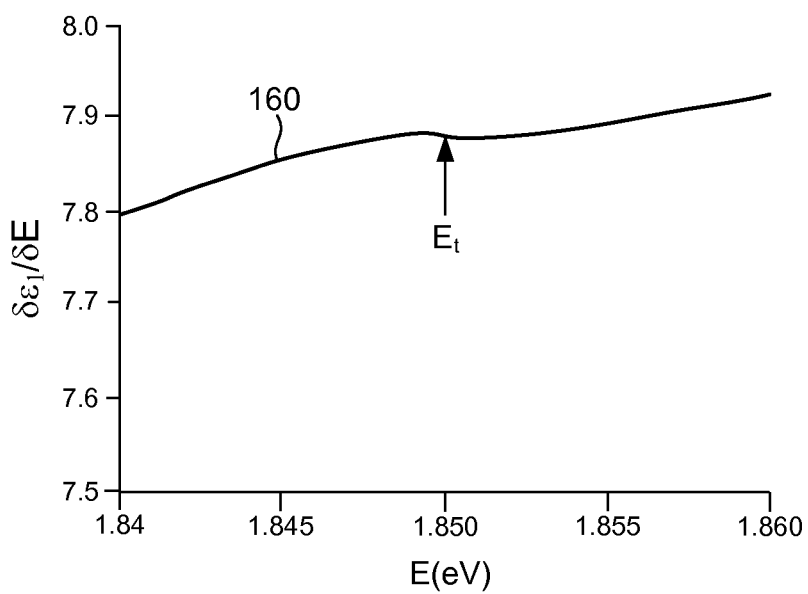
FIG. 7 is a plot illustrative of the first derivative of the real part of the dielectric function of a thin film sample based on a continuous Cody-Lorentz model having no discontinuity over the region 142 highlighted in FIG. 5.

FIG. 7 illustrates a plot 160 of the derivative of the real part of the dielectric function, $\delta\in_1/\delta E$, derived based on the continuous Cody-Lorentz model formulation as described herein over the same region highlighted by dashed circle 142. As illustrated in FIG. 7, the derivative is continuous at the transition energy, $E_t$.

The optical function described by Equations (1)-(6) is a continuous function with continuous derivatives, and is thus, physically reasonable. In addition, maintaining Kramers-Kronig consistency between the real and imaginary parts of the optical dispersion model ensures that the functions defined by the model are physically meaningful. Reformulating the optical function enforcing Kramers-Kronig consistency (e.g., Equations (1)-(6)) into a closed form analytical expression (e.g., Equation (8)) allows for more rapid computation. In addition, the parametric derivatives of the optical function can be found in closed form. The availability of closed form expressions for the optical function and its derivatives is required to perform efficient, effective regression calculations. The model defines six fitting parameters that are related to measurable values such as the optical gap, the maximum (peak) energy, and half width of the absorption band. Therefore, the derived optical functions represent features (e.g., structural, optical, etc.) of the high-K layers that can be used to directly monitor important parameters; band gap, in particular. Thus, parameter values of the optical dispersion model resolved based on measured data can be directly used to determine structural and optical features of high-K dielectric layers, and can also be used to control fabrication processes.

In a further aspect, a band structure characteristic indicative of an electrical performance of the measured layer, or stack of layers, is determined based at least in part on the parameter values of the continuous Cody-Lorentz model of the multi-layer semiconductor wafer. As discussed hereinbefore, the parameters of the model, e.g., $\{E_g, E_p, A, E_0, \Gamma, E_t\}$, are not just fitting parameters, but are related to physically measurable values. For example, $E_g$ represents the band gap energy.

Figure 8:
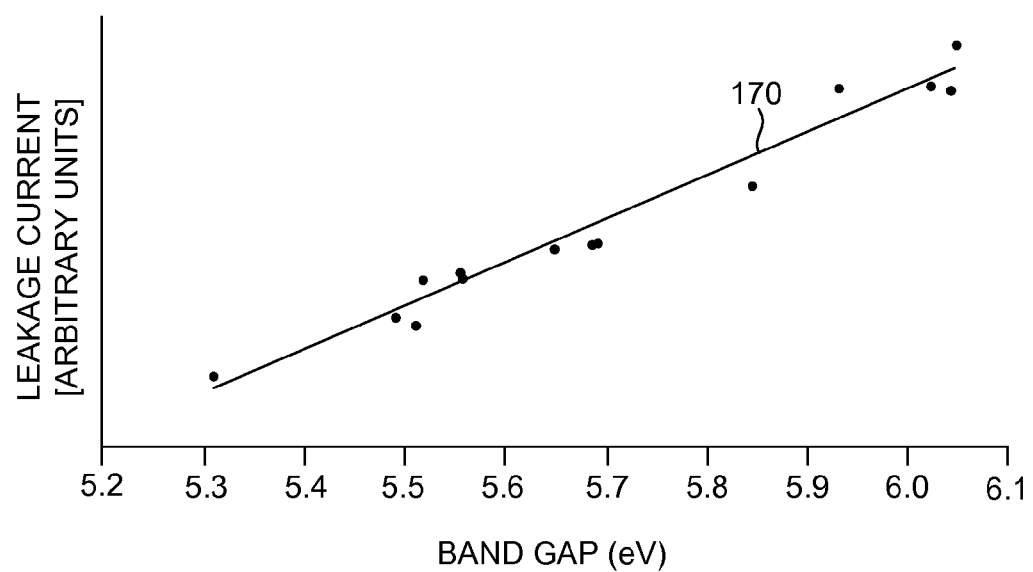
FIG. 8 is a plot illustrative of the correlation between the band gap estimated based on a continuous Cody-Lorentz model and gate stack leakage current.

In one example, the continuous Cody-Lorentz model described herein can be applied to monitor band gap of high-K dielectric stacks. Moreover, the determined band gap is highly correlated to the electrical performance test results of high-K metal gate stacks. FIG. 8 is a plot illustrative of the correlation between the fitted band gap and gate stack leakage current for a number of measured data points. As depicted in FIG. 8, the coefficient of determination, R2, of the linear fit is greater than 0.96, indicating a high correlation between the band gap determined by a fit of the continuous Cody-Lorentz model to measured SE data and measured leakage current.

The data presented in FIG. 8 demonstrates that the continuous Cody-Lorentz model described herein can be used to determine band gap estimates based on measured data that accurately predict the leakage current of semiconductor gate stacks before the semiconductor device is fully fabricated. In addition to silicon based semiconductor devices, similar results may be obtained for a variety of semiconductor devices based on Germanium Silicon and other narrow-gap semiconductors.

The aforementioned examples are provided for illustration purposes and do not limit the type of band structure characteristics that may be contemplated. Many other band structure characteristics that correlate with the electrical properties, and thus act as effective indicators of the electrical performance of a finished wafer, may be contemplated.

In one embodiment, the optical dispersion model described with reference to Equations (1)-(6) has been implemented in the Film Thickness Measurement Library (FTML) of the Off-line Spectral Analysis (OLSA) stand-alone software designed to complement thin film measurement systems such as the Aleris 8510 available from KLA-Tencor Corporation, Milpitas, Calif. (USA). Measurements performed on test samples including high-K gate dielectric stacks showed high precision and reliability at high throughput. In some examples, improved fitting of ellipsometric data with a 2-3 times improvement in throughput was observed in comparison to existing methods.

In block 203, the plurality of parameter values of the optical dispersion model determined from a fitting of measurement data to the continuous Cody-Lorentz model are stored in a memory (e.g., a memory of carrier medium 118). The stored values may be used, for example, to perform further analysis of the specimen, or to control manufacturing process parameters.

In another further aspect, device performance is improved by controlling a process of manufacture of the semiconductor wafer based at least in part on the identified band structure characteristic. In one example, film thickness may be controlled based on band structure characteristics identified from the parameter values of the optical dispersion model illustrated in Equations (1)-(6).

Although, the continuous Cody-Lorentz model is described with reference to modeling of high-K dielectric layers, the model can be applied to other materials. In some examples, the model can be configured to describe the band structure of a variety of nanostructures (e.g., nanowires, quantum dots and quantum wells), including any number of bands of any origin, such as excitonic states. The model can be generalized to include any number of defect levels. In another example, the model can be applied to nanostructures (e.g., quantum wells, quantum dots and nanowires) embedded in another amorphous dielectric slab or layer.

In another further aspect, separate determinations of optical dispersion metrics and band structure characteristics associated with different layers of a wafer can be made based on the same spectral response data. For example, a wafer under measurement may include a semiconductor substrate 112, an intermediate layer 114B, a high-k insulative layer 114A, and an additional film layer (not shown). The spectral response data received from spectrometer 104 includes contributions from all of these layers. A stack layer model that captures the contributions of each of these layers can be used to separately determine band structure characteristics associated with each different physical layer or group of physical layers under analysis.

In another further aspect, the stack model includes a model of the intrinsic absorption peaks of the semiconductor substrate 112 (e.g., silicon). In one example, the intrinsic absorption peaks are accounted for in the spectral measurement of the high-k film. In this manner, the absorption peaks of the semiconductor substrate may be effectively removed from the spectral response of the high-k film. By isolating the spectral response of the high-k film from the semiconductor substrate, a more accurate determination of defects and band structure characteristics associated with the high-k film layer is achieved.

In another further aspect, band structure characteristics (e.g., band gap and defects) are used to grade wafers and microchips early in the production process based on the quality of the gate insulator. This may avoid the need to grade wafers and microchips at the end of the production process using expensive and time consuming electrical test equipment.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

A typical semiconductor process includes wafer processing by lot. As used herein a "lot" is a group of wafers (e.g., group of 25 wafers) which are processed together. Each wafer in the lot is comprised of many exposure fields from the lithography processing tools (e.g. steppers, scanners, etc.). Within each field may exist multiple die. A die is the functional unit which eventually becomes a single chip. One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the embodiments may be used for characterizing thin films of another specimen such as a reticle, which may also be commonly referred to as a mask or a photomask. Many different types of reticles are known in the art, and the terms "reticle," "mask," and "photomask" as used herein are intended to encompass all types of reticles known in the art.

Although embodiments are described herein with respect to measurement of thin films applied to wafers, it is to be understood that the methods and systems disclosed herein may be used for characterizing critical dimensions of semiconductor structures, overlay among layers of semiconductor structures, and material composition of semiconductor structures.

The embodiments described herein generally relate to methods for determining band structure characteristics of multi-layer thin films based on optical model parameter values at high throughput. For example, one embodiment relates to a computer-implemented method for determining band structure characteristics of multi-layer thin films based on optical model parameter values derived from spectroscopic ellipsometer data. However, the methods described herein are not limited in the types of inspection systems from which optical model parameter values may be derived. For example, in one embodiment, the inspection system includes a reflectometer for thin film inspection of the wafer. In general, the optical dispersion models described herein may be applied to the analysis of measurement data received from a variety of broadband and narrowband metrology tools. For example, spectroscopic ellipsometers and reflectometers, multi-angle ellipsometers and reflectometers, including any number or type of illumination sources (e.g., lamp or laser based sources emitting light in the visible, infra-red, ultra-violet, vacuum ultraviolet, deep ultraviolet spectrums) may be contemplated within the scope of this patent document.

In addition, the inspection system may be configured for inspection of patterned wafers and/or unpatterned wafers. The inspection system may be configured as a LED inspection tool, edge inspection tool, backside inspection tool, macro-inspection tool, or multi-mode inspection tool (involving data from one or more platforms simultaneously), and any other metrology or inspection tool that benefits from the determination of band structure characteristics of multi-layer thin films based on optical model parameter values at high throughput.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A non-transitory, computer-readable medium, comprising:
code for causing a computer to receive a spectral response of an unfinished, multi-layer semiconductor wafer across a spectral range;
code for causing the computer to determine a plurality of parameter values of an optical dispersion model of one or more layers of the multi-layer semiconductor wafer based at least in part on the spectral response, wherein the optical dispersion model includes a Cody-Lorentz model having a first derivative of a dielectric function with respect to energy that is continuous at the Urbach transition energy of the Cody-Lorentz model, wherein the rate of attenuation of the Urbach function, $E_u$, is defined as $$E_u = \frac{E_1}{\partial E_1 / \partial E_t} = \frac{E_1}{D},$$

wherein $$D = \frac{E_0^4 - E_t^4}{(E_0^2 - E_t^2)^2 + \Gamma^2 E_t^2} + \frac{E_p^2}{(E_t - E_g)^2 + E_p^2} \cdot \frac{E_t}{E_t - E_g};$$

and wherein $E_t$, is the demarcation energy, $E_0$, is the resonant energy of a Lorentz function, $E_g$, is the band gap energy, $E_p$, is the transition energy, and $\Gamma$, is the width of the Lorentz function; and
code for causing the computer to store the plurality of parameter values of the optical dispersion model in a memory.

2. The non-transitory, computer-readable medium of claim 1, wherein the optical dispersion model is sensitive to a band gap of a layer of the unfinished, multi-layer semiconductor wafer.

3. The non-transitory, computer-readable medium of claim 1, further comprising:
code for causing the computer to determine a band structure characteristic indicative of an electrical performance of a first layer of the multi-layer semiconductor wafer based at least in part on parameter values of the optical dispersion model of the multi-layer semiconductor wafer.

4. The non-transitory, computer-readable medium of claim 3, wherein the electrical performance of the multi-layer semiconductor wafer is any of an equivalent oxide thickness (EOT), a leakage current, a threshold voltage, and a breakdown voltage.

5. The non-transitory, computer-readable medium of claim 3, further comprising:
code for causing the computer to control a process of manufacture of the unfinished, multi-layer semiconductor wafer based at least in part on the band structure characteristic.

6. The non-transitory, computer-readable medium of claim 1, wherein the one or more layers include at least one nanostructure.

7. The non-transitory, computer-readable medium of claim 6, wherein the at least one nanostructure is any of a plurality of quantum dots, a plurality of nanowires, and a plurality of quantum wells.

8. The non-transitory, computer-readable medium of claim 1, wherein a first layer of the one or more layers is an electrically insulative layer disposed above a semiconductor substrate.

9. The non-transitory, computer-readable medium of claim 8, wherein the first layer includes an intermediate layer between the semiconductor substrate and the electrically insulative layer.

10. The non-transitory, computer-readable medium of claim 1, further comprising:
code for causing the computer to determine the spectral response of the unfinished, multi-layer semiconductor wafer based on a measurement of the multi-layer semiconductor wafer with either an ellipsometer or a reflectometer.

11. A system comprising:

an illuminator;

a spectrometer; and one or more computer systems configured to:

receive a spectral response of an unfinished, multi-layer semiconductor wafer across a spectral range;

determine a plurality of parameter values of an optical dispersion model of one or more layers of the multi-layer semiconductor wafer based at least in part on the spectral response, wherein the optical dispersion model includes a Cody-Lorentz model having a first derivative of a dielectric function with respect to energy that is continuous at the Urbach transition energy of the Cody-Lorentz model, wherein the rate of attenuation of the Urbach function, $E_u$, is defined as $$E_u = \frac{E_1}{\partial E_1 / \partial E_t} = \frac{E_1}{D},$$

wherein $$D = \frac{E_0^4 - E_t^4}{(E_0^2 - E_t^2)^2 + \Gamma^2 E_t^2} + \frac{E_p^2}{(E_t - E_g)^2 + E_p^2} \cdot \frac{E_t}{E_t - E_g};$$

and wherein $E_t$ is the demarcation energy, $E_0$ is the resonant energy of a Lorentz function, $E_g$ is the band gap energy, $E_p$ is the transition energy, and $\Gamma$, is the width of the Lorentz function; and store the plurality of parameter values of the optical dispersion model in a memory.

12. The system of claim 11, wherein the optical dispersion model is sensitive to a band gap of a layer of the unfinished, multi-layer semiconductor wafer.

13. The system of claim 11, wherein the one or more computer systems are further configured to:

determine a band structure characteristic indicative of an electrical performance of a first layer of the multi-layer semiconductor wafer based at least in part on parameter values of the optical dispersion model of the multi-layer semiconductor wafer.

14. The system of claim 13, wherein the electrical performance of the multi-layer semiconductor wafer is any of an equivalent oxide thickness (EOT), a leakage current, a threshold voltage, and a breakdown voltage.

15. The system of claim 13, wherein the one or more computer systems are further configured to:

control a process of manufacture of the unfinished, multi-layer semiconductor wafer based at least in part on the band structure characteristic.

16. The system of claim 11, wherein the one or more layers include at least one nanostructure.

17. The system of claim 16, wherein the at least one nanostructure is any of a plurality of quantum dots, a plurality of nanowires, and a plurality of quantum wells.

18. The system of claim 11, wherein a first layer of the one or more layers is an electrically insulative layer disposed above a semiconductor substrate.

19. The system of claim 18, wherein the first layer includes an intermediate layer between the semiconductor substrate and the electrically insulative layer.

20. The system of claim 11, wherein the one or more computer systems are further configured to:

determine the spectral response of the unfinished, multi-layer semiconductor wafer based on a measurement of the multi-layer semiconductor wafer with either an ellipsometer or a reflectometer.

* * * * *